US012746112B2

(12) United States Patent
Mangum

(10) Patent No.: US 12,746,112 B2
(45) Date of Patent: Sep. 29, 2026

(54) METHOD AND APPARATUS FOR ADHERING A CAPSULAR BAG TO AN INTRAOCULAR LENS

(71) Applicant: Alcon Inc., Fribourg (CH)

(72) Inventor: Michael Lee Mangum, Sunnyvale, CA (US)

(73) Assignee: Alcon Inc., Fribourg (CH)

(*) Notice: Subject to any disclaimer, the term of this patent is extended or adjusted under 35 U.S.C. 154(b) by 82 days.

(21) Appl. No.: 16/223,348

(22) Filed: Dec. 18, 2018

(65) Prior Publication Data

US 2019/0183638 A1 Jun. 20, 2019

Related U.S. Application Data

(60) Provisional application No. 62/599,992, filed on Dec. 18, 2017.

(51) Int. Cl.
*A61F 2/16* (2006.01)
*A61F 9/008* (2006.01)

(52) U.S. Cl.
CPC ............ *A61F 2/1662* (2013.01); *A61F 9/008* (2013.01); *A61F 9/00812* (2013.01); *A61F 2002/16901* (2015.04); *A61F 2009/00844* (2013.01); *A61F 2009/0087* (2013.01); *A61F 2009/00897* (2013.01); *A61F 2210/0076* (2013.01)

(58) Field of Classification Search
CPC .... A61F 2/1662; A61F 9/00812; A61F 9/008; A61F 2009/00897; A61F 2009/00844; A61F 2009/0087; A61F 2210/0076; A61F 2002/16901
USPC ........................................................ 606/2–19
See application file for complete search history.

(56) References Cited

U.S. PATENT DOCUMENTS

2009/0171327 A1* 7/2009 Kurtz .................. A61F 9/00838 606/6
2010/0082017 A1* 4/2010 Zickler ..................... A61F 2/16 606/4
2013/0172861 A1 7/2013 Youssefi
(Continued)

FOREIGN PATENT DOCUMENTS

DE 102014012631 A1 2/2016
WO WO-9635398 A1 * 11/1996 ........... A61F 2/1613
(Continued)

OTHER PUBLICATIONS

Susanne Krag, Carl Christian Danielsen & Troels T. Andreassen (1998) Thermal and mechanical stability of the lens capsule, Current Eye Research, 17:5, 470-477, DOI: 10.1076/ceyr.17.5.470.5198 (Year: 1998).*
(Continued)

*Primary Examiner* — Jennifer Pitrak McDonald
*Assistant Examiner* — Shreya Anjaria
(74) *Attorney, Agent, or Firm* — PATTERSON + SHERIDAN, LLP

(57) ABSTRACT

A method for performing an ophthalmic procedure on an eye, the eye having a capsular bag in which an intraocular lens (IOL) has been implanted, includes applying energy to a portion of the capsular bag. The applied energy is sufficient to melt the portion of the capsular bag without cauterization such that the portion of the capsular bag adheres to an adjacent portion of the IOL.

10 Claims, 6 Drawing Sheets

(56) References Cited

U.S. PATENT DOCUMENTS

| | | | | |
|---|---|---|---|---|
| 2014/0194860 A1* | 7/2014 | Dick | .................. | A61F 9/00825 606/6 |
| 2014/0350533 A1* | 11/2014 | Horvath | ............. | A61F 9/00825 606/6 |
| 2015/0265398 A1* | 9/2015 | Hartkens | ............. | A61F 9/00821 606/4 |
| 2017/0252148 A1* | 9/2017 | Cumming | ............. | A61F 2/1629 |
| 2018/0271646 A1* | 9/2018 | Marcos Celestino | ........................ | A61F 2/1624 |

FOREIGN PATENT DOCUMENTS

| | | | | |
|---|---|---|---|---|
| WO | WO-2011085349 A2 * | 7/2011 | ........... | A61F 2/0077 |
| WO | WO-2017079449 A1 * | 5/2017 | ........... | A61F 2/1662 |
| WO | WO-2017079733 A1 * | 5/2017 | ........... | A61F 2/1601 |

OTHER PUBLICATIONS

Susana Marcos, Nicolas Alejandre, Jorge Lamela, Carlos Dorronsoro, Irene E. Kochevar; Toward New Engagement Paradigms for Intraocular Lenses: Light-Initiated Bonding of Capsular Bag to Lens Materials. Invest. Ophthalmol. Vis. Sci. 2015;56(8):4249-4256. doi: https://doi.org/10.1167/iovs.15-17070 (Year: 2015).*

Matteini, Paolo & Rossi, Francesca & Ratto, Fulvio & Pini, Roberto. (2010). Laser Welding of Biological Tissue: Mechanisms, Applications and Perspectives. 10.1002/9783527632053.ch9. (Year: 2010).*

* cited by examiner

350A

350B

350C

350D

METHOD AND APPARATUS FOR ADHERING A CAPSULAR BAG TO AN INTRAOCULAR LENS

CROSS-REFERENCE TO RELATED APPLICATIONS

This application claims the benefit of priority of U.S. Provisional Patent Application Ser. No. 62/599,992 titled "METHOD AND APPARATUS FOR ADHERING A CAPSULAR BAG TO AN INTRAOCULAR LENS," filed on Dec. 18, 2017, which is hereby incorporated by reference in its entirety as though fully and completely set forth herein.

FIELD

This present disclosure relates generally ophthalmic lenses and, more particularly, to a method and apparatus for adhering a capsular bag to an intraocular lens.

BACKGROUND

Intraocular lenses (IOLs) may be implanted in patients' eyes to replace a patient's natural lens. An IOL typically includes (1) an optic that corrects the patient's vision (e.g., typically via refraction or diffraction), and (2) haptics that constitute support structures that hold the optic in place within the patient's eye (e.g., within capsular bag). In general, a physician selects an IOL for which the optic has the appropriate corrective characteristics for the patient. During ophthalmic surgery, often performed for conditions such as cataracts, the surgeon implants selected IOL by making an incision in the capsular bag of the patient's eye (a capsulorhexis) and inserting the IOL through the incision. Typically, the IOL is folded for insertion into the capsular bag via a corneal incision and unfolded once in place within the capsular bag. During unfolding, the haptics may expand such that a small section of each bears on the capsular bag, retaining the IOL in place.

Although existing IOLs may function acceptably well in many patients, they also have certain shortcomings. For example, existing IOL designs may result in posterior capsule opacification (PCO), a condition in which residual lens epithelial cells from the equator of the capsular bag migrating inward along the posterior side of the capsular bag towards the optic. Because the cell growth may opacify the posterior surface of the capsular bag, PCO may negatively impact the patient's vision. Certain current IOL design attempt to address PCO by adding a sharp edge around the posterior surface of the optic. Although such sharp edges may inhibit the migration of lens epithelial cells, they generally do not completely eliminate PCO. Once PCO has occurred, it may be addressed via a laser procedure called a posterior capsulotomy in which the opacification is removed by creating an opening in the posterior surface of the capsule. The added cost, time, and risk to the patient associated with a posterior capsulotomy may make the procedure undesirable.

Accordingly, what is needed is an improved mechanism that may address PCO.

SUMMARY

A method for performing an ophthalmic procedure on an eye, the eye having a capsular bag in which an intraocular lens (IOL) has been implanted, includes applying energy to a portion of the capsular bag. The applied energy is sufficient to melt the portion of the capsular bag without cauterization such that the portion of the capsular bag adheres to an adjacent portion of the IOL.

In certain embodiments, the above-described ophthalmic procedure may provide one or more technical advantages. For example, the above-described ophthalmic procedure may result in the capsular bag being adhered to the IOL around an entire periphery of the optic, thereby forming a seal between the capsular bag and the IOL. As a result, lens epithelial cells may be prevented from migrating along the optic from the equatorial region of the capsular bag, thereby reducing or eliminating the incidence of PCO. Moreover, because the seal is created on the haptics and/or periphery of the optic (i.e., outside the patient's optical path), the above described PCO reduction/elimination may be achieved without significantly adversely affecting the patient's vision. As another example, the above-described ophthalmic procedure may result in the capsular bag being adhered to the IOL around a sufficient portion of the IOL to ensure the IOL is stable against rotations or other undesirable motion. Because rotational stability may be particularly important for certain types of IOLs (e.g., toric IOLs), the above-described ophthalmic procedure, by increasing stability, may result in better patient outcomes.

BRIEF DESCRIPTION OF SEVERAL VIEWS OF THE DRAWINGS

For a more complete understanding of the present disclosure and the advantages thereof, reference is now made to the following description taken in conjunction with the accompanying drawings in which like reference numerals indicate like features and wherein.

Figure 1:
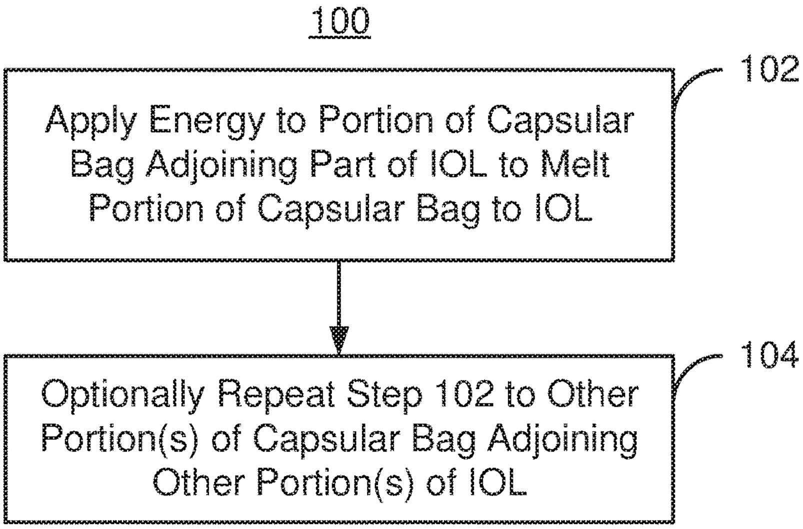
FIG. 1 is a flow chart depicting an exemplary embodiment of a method for performing an ophthalmic procedure that adheres a capsular bag to an IOL.

The skilled person in the art will understand that the drawings, described below, are for illustration purposes only. The drawings are not intended to limit the scope of the applicant's disclosure in any way.

DETAILED DESCRIPTION

The exemplary embodiments relate to mechanisms for sealing a portion of the capsular bag to a portion of the intraocular lens (IOL). The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments as well as to multiple embodiments. The embodiments will be described with respect to systems and/or devices having certain components. However, the systems and/or devices may include more or less components than those shown, and variations in the arrangement and type of the components may be made without departing from the scope of the invention. Further, although specific blocks are depicted, various functions of the blocks may be separated into different blocks or combined. The exemplary embodiments will also be described in the context of particular methods having certain steps. However, the method and system operate effectively for other methods having different and/or additional steps and steps in different orders that are not inconsistent with the exemplary embodiments. Thus, the present invention is not intended to be limited to the embodiments shown, but is to be accorded the widest scope consistent with the principles and features described herein.

The method and system are also described in terms of singular items rather than plural items. One of ordinary skill in the art will recognize that these singular terms encompass plural. For example, a step that is described as melting a portion of the capsular bag may melt multiple contiguous or noncontiguous sections of the capsular bag. In certain embodiments, the system includes one or more processors and a memory. The one or more processors may be configured to execute instructions stored in the memory to cause and control the process set forth in the drawings and described below. As used herein, a processor may include one or more microprocessors, field-programmable gate arrays (FPGAs), controllers, or any other suitable computing devices or resources, and memory may take the form of volatile or non-volatile memory including, without limitation, magnetic media, optical media, random access memory (RAM), read-only memory (ROM), removable media, or any other suitable memory component. Memory may store instructions for programs and algorithms that, when executed by a processor, implement the functionality described herein with respect to any such processor, memory, or component that includes processing functionality. Further, aspects of the method and system may take the form of an entirely hardware embodiment, an entirely software embodiment (including firmware, resident software, micro-code, etc.) or an embodiment combining software and hardware aspects. Aspects of the method and system may take the form of a software component(s) executed on at least one processor and which may be embodied in one or more computer readable medium(s) having computer readable program code embodied thereon.

In general, the present disclosure relates to an ophthalmic procedure performed in conjunction with a cataract procedure in which an IOL has been implanted in capsular bag of a patient's eye. More particularly, the procedure involves applying energy to a portion of the capsular bag (e.g., by firing a laser at the portion of the capsular bag) after the IOL has been implanted. The applied energy may be sufficient to melt the portion of the capsular bag without cauterization such that the portion of the capsular bag adheres to a peripheral portion of the IOL. Adhering the capsular bag to the IOL may inhibit the migration of lens epithelial cells from the equatorial region of the capsular bag toward the optical axis, thereby reducing or eliminating the incidence of PCO. Additionally, adhering the capsular bag to the IOL may increase the rotational stability of the IOL, which may be important for certain types of IOLs (e.g., toric IOLs).

FIG. 1 is a flow chart depicting an exemplary embodiment of a method 100 for performing an ophthalmic procedure that adheres a capsular bag to an IOL. For simplicity, some steps may be omitted, interleaved, performed in another order and/or combined. The method 100 may include executing instructions on one or more processors and/or actions by an individual such as a physician. Further, the method 100 is described in the context of a non-invasive procedure (e.g., a separate procedure performed after the cataract procedure). However, the method 100 may be alternatively be performed as part of the cataract procedure.

The method 100 generally commences after an IOL has been implanted in the capsular bag of a patient's eye. In some embodiments, the method 100 may start a sufficient time after IOL implantation such that the patient's eye has healed and the environment in which the IOL resides has reached an equilibrium. For example, in such an embodiment, the method 100 may begin after the capsular bag has had an opportunity to collapse/seal around the IOL. In some embodiments, the method 100 occurs between forty-eight hours and two weeks after the IOL implantation (e.g., during a follow-up visit for the patient).

The implanted IOL typically includes an optic and one or more support structures referred to herein as haptics. In some embodiments, the optic and haptics may be formed of the same material. In other embodiments, the optic and haptics may be formed of different materials. The optic forms the lens through which the patient sees. The haptics aid in maintaining the IOL in place within the capsular bag. For example, the haptics may bear on and/or be bonded to the capsular bag using the method 100.

The IOL may include one or more mechanisms to facilitate the method 100. In certain embodiments, the haptics and/or a periphery of the optic may have a coating that improves the bonding of the melted portion of the capsular bag to the IOL. As one particular example, the haptics and/or a periphery of the optic may have a coating of Rose bengal, which may increase adherence when irradiated with certain wavelengths of laser light (e.g., green laser). In certain embodiments, the haptics and/or a periphery of the optic may include ridges or another textured feature that provides greater surface area or another mechanism for improving the adhesion between the melted portions of the capsular bag and the IOL. In certain embodiments, all or a portion of the IOL may be formed of a material selected to improve the adhesion between the IOL and the melted portion of the capsular bag. For example, some or all of the IOL may be formed of a non-hydrophobic material that is more likely to allow better adhesion of the collagen of the capsular bag to the IOL.

Energy is applied to a portion of the capsular bag adjacent to a portion of the IOL, via step 102. For example, energy may be applied to part(s) of the capsular bag that are in proximity to or in physical contact with selected portion(s) of the optic and/or haptics. The energy applied in step 102 may be sufficient to melt the portion of the capsular bag without cauterization and, therefore, without forming a hole in the capsular bag. The melted portion of the capsular bag may adhere to the adjacent portion of the IOL. In certain embodiments, energy may be applied to parts of the capsular bag adjacent to the haptics and/or periphery of the optic such that the melted portion of the capsular bag is not within the patient's optical path and quality of vision is not negatively impacted.

The capsular bag is formed mainly of collagen (Type IV collagen). Type IV collagen has multiple melting points. The specific temperatures of the melting points may depend upon the age of the patient or other factors. In step 102, the portion of the capsular bag desired to be melted may receive enough energy to raise its temperature to a target temperature or target temperature range. For example, the temperature may be raised to at or near the lowest melting temperature, between the lowest and the middle melting temperatures or to another temperature that allows for reflow of the melted collagen without compromising the capsular bag's structural integrity.

In certain embodiments, step 102 may further include determining the local temperature to which each portion of the capsular bag is desired to be raised as well as the amount of energy required to achieve that temperature in the desired volume (portion) of the capsular bag. Because the melting temperatures may depend upon the age of the patient, the local temperature desired for melting the capsular bag may also be determined based on factors specific to the patient. Alternatively, these and other variables relevant to the method 100 may be determined prior to the start of the method 100.

In certain embodiments, the energy applied at step 102 is provided using a laser. For example, a neodymium-doped yttrium aluminum garnet (Nd:YAG) laser may be utilized. Such a laser may provide pulses having a duration in the femtosecond regime. In other embodiments, another laser or energy source may be used. The energy provided by the laser may be controlled by some combination of spot size (the incident area), irradiance (energy per unit area), laser power, duration of the pulse and/or time the region is illuminated. By changing the pulse duration, time illuminated or spot size, the energy provided to the desired region may be controlled. Thus, step 102 may include determining the desired energy to be applied to each region, focusing the laser to the desired spot size on that portion of the capsular bag, and firing the laser for the appropriate interval to deliver the desired energy to the portion(s) of the capsular bag.

Step 102 is optionally repeated until all desired portions of the capsular bag are bonded with the desired portions of the IOL, via step 104. For example, step 102 may only melt and, therefore, adhere a small region of the capsular bag to the IOL. In such a case, step 104 can repeat step 102 at one or more additional locations. The selected seal between the capsular bag and the IOL may be formed.

In certain embodiments, method 100 may provide one or more technical advantages. For example, method 100 may result in the capsular bag being adhered to the IOL around an entire periphery of the optic, thereby forming a seal between the capsular bag and the IOL. As a result, lens epithelial cells may be prevented from migrating along the optic from the equatorial region of the capsular bag, thereby reducing or eliminating the incidence of PCO. Moreover, because the seal is created on the haptics and/or periphery of the optic (i.e., outside the patient's optical path), the above described PCO reduction/elimination may be achieved without significantly adversely affecting the patient's vision. As another example, method 100 may result in the capsular bag being adhered to the IOL around a sufficient portion of the IOL to ensure the IOL is stable against rotations or other undesirable motion. Because rotational stability may be particularly important for certain types of IOLs (e.g., toric IOLs), method 100, by increasing stability, may result in better patient outcomes.

Figure 2:
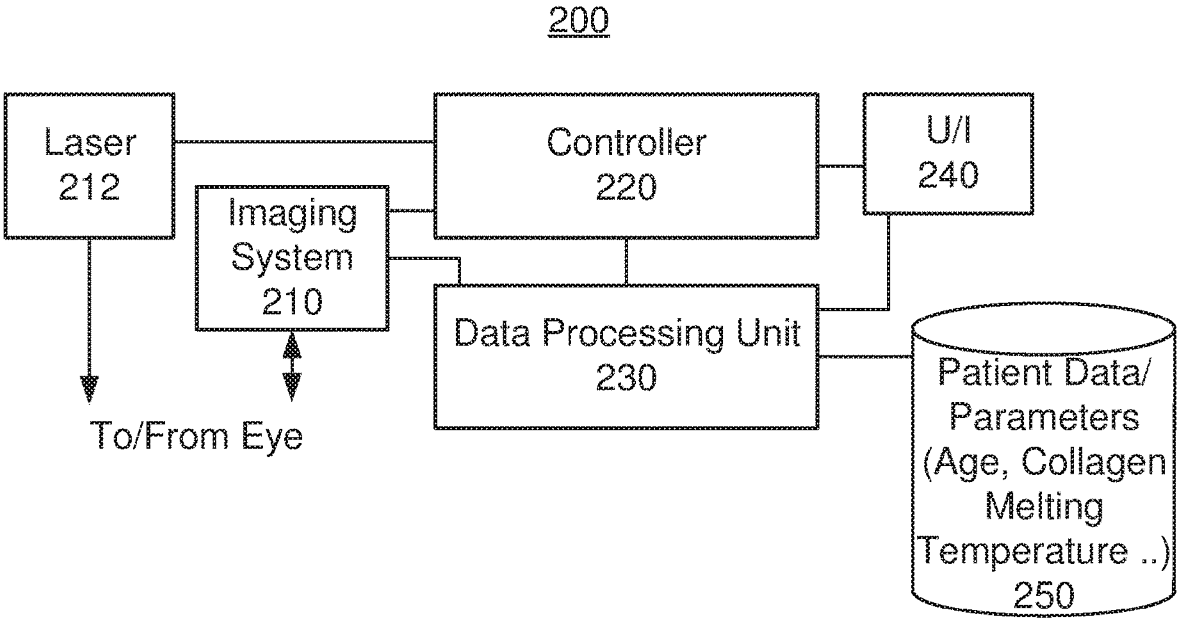
FIG. 2 is a block diagram of an exemplary embodiment of an apparatus for adhering a capsular bag to the IOL.

FIG. 2 is a block diagram of an exemplary embodiment of an apparatus 200 for adhering a capsular bag to an IOL. The apparatus 200 may include an imaging system 210, a laser 212, a controller 220, a data processing unit 230, a user interface (U/I) 240, and a data store 250 including any patient data, parameters and other information. For simplicity, only some components are shown. In addition, the components depicted in FIG. 2 may be packaged together in a single apparatus. Alternatively, certain components, such as portions of imaging system, laser and data processing, may be implemented separately. Further, the components may be implemented in hardware and/or software. The method 100 may be implemented using the system 200.

The imaging system 210 may include a camera and/or other image capture device that may be managed using the controller 220. In some embodiments, step 102 may include the controller 220 managing the focusing and magnification of the eye. Thus, the imaging system may or may not include a microscope or other magnification that allows for enhanced detail. In other embodiments, other components may be used in for the imaging system 210. Such imaging systems 210 may or may not provide three-dimensional data for the eye. In some embodiments, video camera(s) or other mechanism for showing the progression of time may be part of the image(s) received. Further, the resolution of the imaging system 210 is sufficient to allow the relevant features of the eye to be determined. Thus, the physician may use the imaging system when implanting the IOL if the method 100 is performed during surgery. If the method 100 is not performed during surgery, then the imaging system 210 may simply allow the physician to better view portions of the patient's eye.

The laser 212 is used to melt portions of the capsular bag. For example, the laser 212 may be a Nd:YAG laser. The U/I 240 allows output to be provided to the physician and input to be received from the physician. For example, the physician may indicate which portion(s) of the capsular bag to be melted using the method 100 and/or may confirm the portion(s) of the capsular bag to be melted that are selected by the controller 220. The U/I 240 provides this confirmation to the data processing unit 230. The U/I 240 may also include a display for rendering image(s) of the eye or providing other visual feedback to the physician. The laser 212 and system 200 might also be used in other procedures not described herein.

The data processing unit 230 may receive image data from the imaging system 210. The data processing unit 230 may also perform some or all of steps 102 and 104. In some embodiments, the data processing unit 230 also accesses the data store 250. For example, the data processing unit 230 may access data related to the patient's age and the melting temperature of Type IV collagen for a patient of that age in order to determine the melting temperature of the capsular bag and/or the amount of energy to be applied using the laser 212.

The controller 220 may communicate with the laser 212, imaging system 220, data processing unit 230, and user interface 240. The controller 220 may manage the operation of laser 212. For example, the control 220 may aim the laser 212, set the spot size of the laser and turn the laser 212 on/off. Using the apparatus 200, therefore, the method 100 may be implemented. One or more of the benefits of the method 100 may thus be achieved.

Figure 3:
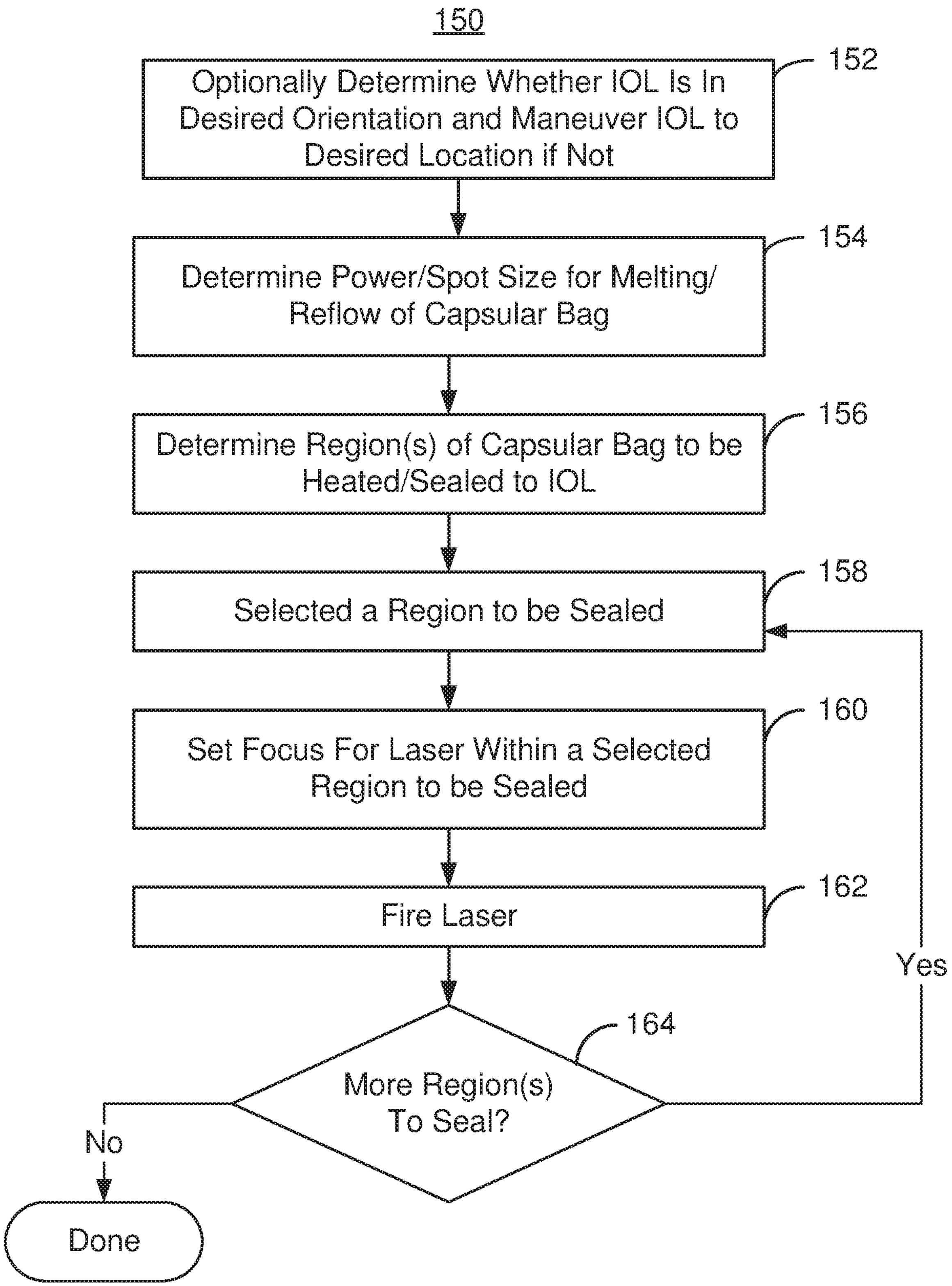
FIG. 3 is a flow chart depicting an exemplary embodiment of a method for performing a non-surgical ophthalmic procedure for adhering a capsular bag to the IOL.

FIG. 3 is a flow chart depicting an exemplary embodiment of a method 150 for performing an ophthalmic procedure that adheres a capsular bag to an IOL. Some steps may be omitted, interleaved, performed in another order and/or combined. The method 150 may include executing instructions on one or more processors. Further, the method 150 is described in the context of the system 200. However, the method 150 may be performed by or using other apparatuses (not shown).

FIGS. 4A-4F depict exemplary embodiments of portions of an eye 300 before and during the method 150. FIGS.

4A-4F are not to scale and only portions of the eye may be shown. A particular patient, condition and/or IOL is not intended to be shown in FIGS. 4A-4F.

Referring to FIGS. 2-4F, FIG. 4A depicts the eye 300 as well as the device to be implanted, IOL 330. The eye 300 is shown as including a cornea 302, capsular bag 304, iris 306, pupil 308, and vitreal cavity 310. Also shown by dashed lines is optical path 312. The optical path 312 includes regions within the eye 300 through which light may travel in order to allow the patient to see. The IOL 330 includes an optic axis 331, a haptics 332, and an optic 334. The optic 334 functions as the lens which may replace the patient's lens. The haptics 332 hold the IOL substantially in place within the capsular bag. Incision(s) used in implanting the IOL 330 into the eye 300 are not shown for clarity.

Figure 4A:
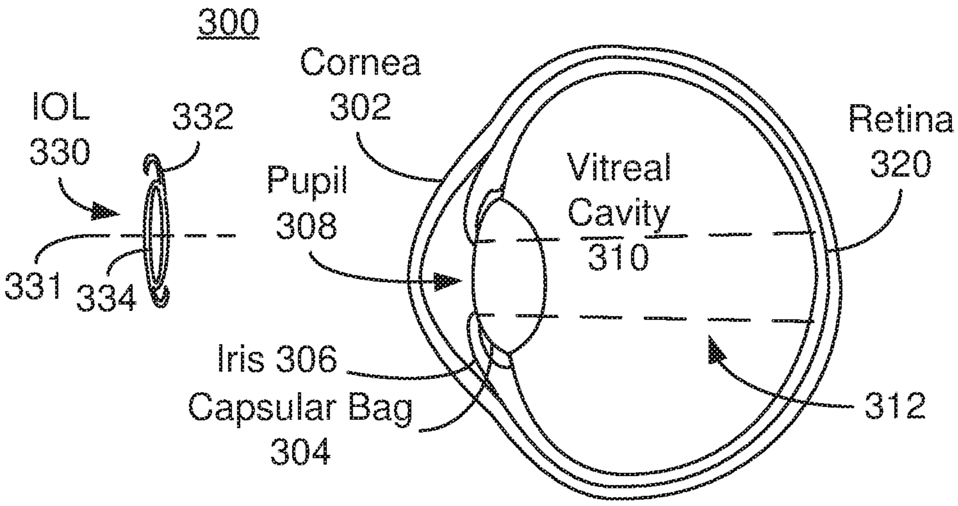
FIGS. 4A-4F depict exemplary embodiments of the eye before and during a non-surgical procedure for adhering the capsular bag to the IOL.
Figure 4B:
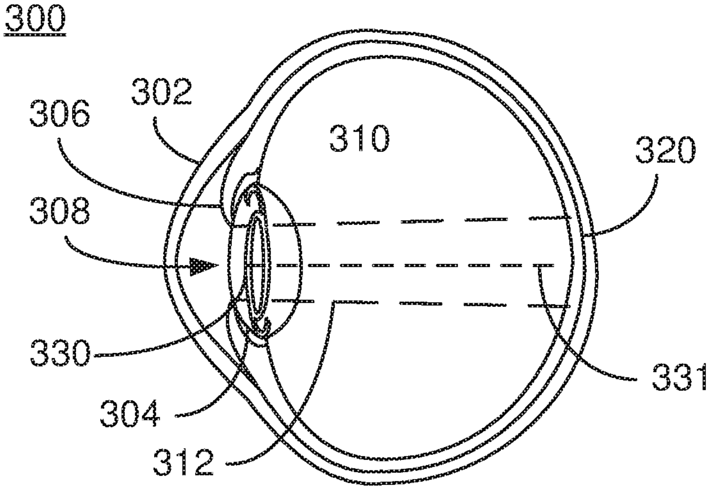
Figure 4C:
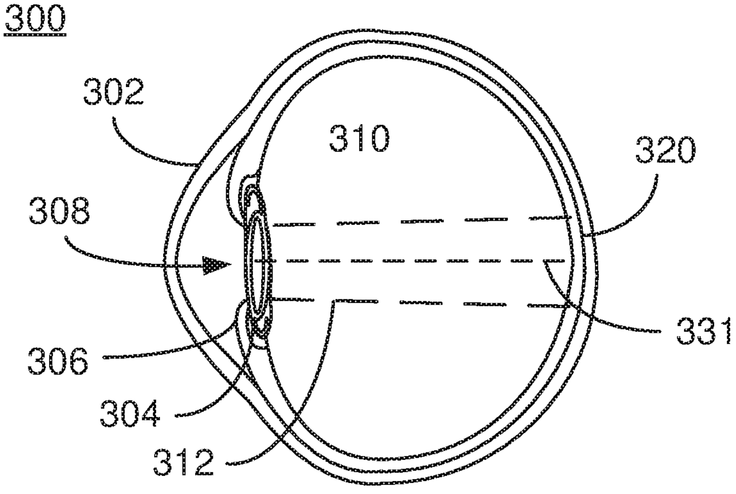

FIG. 4B depicts the eye 300 and the IOL 330 has been placed in capsular bag 304. During implantation, the capsular bag 304 is typically artificially supported by a positive flow of fluid through the eye. Thus the capsular bag 304 is shown as significantly larger than the implanted IOL 330. Although no incision is shown, FIG. 4B may be considered to depict the eye 300 during surgery. The method 150 may commence once the eye 300 is in the situation shown in FIG. 4B. FIG. 4C depicts the eye 300 and IOL 330 after the capsular bag 304 is no longer artificially supported. The volume of the IOL 330 is typically significantly less than that of the natural lens of the patient (not shown). Thus, the capsular bag 304 has collapsed around the IOL 330. The situation shown in FIG. 4C may represent the patient's eye a few days through a few weeks after the surgical procedure that implants the IOL 330 has been completed. Consequently, step the method 150 might also commence once the eye is in the situation shown in FIG. 4C.

In method 150, the physician may determine whether the IOL 330 is in the desired location within the eye 300 and, if not, may maneuver the IOL 330 into the desired location, via step 152. Step 152 may be performed as part of surgery. For example, step 152 may be performed while incision(s) (not shown) are still open and the surgeon can manipulate the IOL.

The energy to be provided by the laser 212 is determined, via step 154. Step 154 may include accessing patient data, such as the patient's age, in the data store 250 and using this information to determine the target temperature(s) for melting a portion of the capsular bag 304. This determination may be made via data processing unit 230. The energy for a laser pulse that corresponds to the target temperature(s) may also be calculated by the data processing unit. The spot size for the laser 212 and duration of each pulse may also be determined by the data processing unit 230.

Figure 4D:
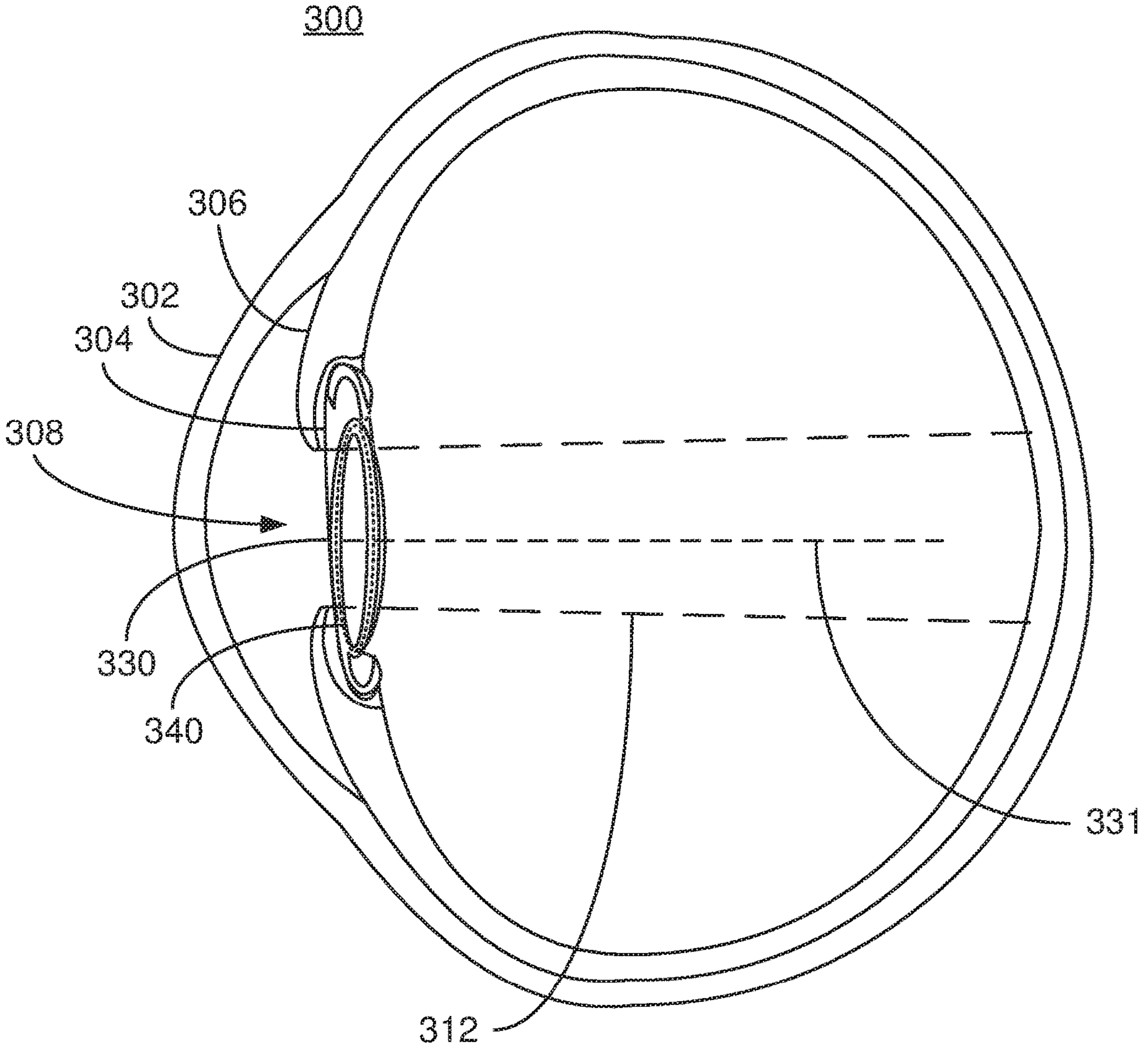

The portions of the capsular bag 304 to be adhered to the IOL 330 are determined, via step 156. Step 156 may include allowing the physician to input whether the optic 334 is desired to be sealed to mitigate PCO or whether the location of the IOL 330 is simply desired to be stabilized by bonding with the capsular bag. The data processing unit 230 may then image the eye 300 and determine the regions of the capsular bag 304 that are in proximity to or in contact with the desired portions of the IOL. Alternatively, the physician may manually select the portions of the capsular bag 304 to be heated. In certain embodiments, the portions of the capsular bag 304 to be heated may be located adjacent the haptics 332 and/or the periphery of the optic 334 of the IOL 330. As a result, the portions of the capsular bag 304 to be heated may be outside of the optical path 312. As one example, FIG. 4D depicts the eye 300 with the IOL 330 in place and the capsular bag 304 collapsed around the IOL 330. Also shown by a dashed line are the portions 340 of the capsular bag desired to be heated. For the embodiment depicted in FIG. 4D, the periphery of the posterior surface of the optic 334 is desired to be adhered to the capsular bag 304.

A particular region of the capsular bag 304 to be heated next is selected, via step 158. Step 158 may be performed automatically by the system 200 or may be selected manually by the physician. The laser 212 may be focused to target the selected region of the capsular bag 304, via step 160. The data processing unit 230 may provide the region and controller 210 may target the laser 212 in step 160. As part of step 160, the controller 210 may set the pulse duration and spot size determined in strep 154. Alternatively, step 160 may be performed manually by the physician.

The laser 212 may be fired at the target region for the desired time with one or more pulses of the desired duration, via step 162. Thus the desired energy is provided to the selected portion of the capsular bag 304. The energy applied in step 162 may be sufficient to melt the portion of the capsular bag 304 without cauterization without forming an aperture in the capsular bag 304. The melted portion of the capsular bag 304 may adhere to the selected portion of the IOL 330.

It is determined whether there are additional regions of the capsular bag 304 to heat, via step 164. If not, the method 150 has completed. If so, another region is selected in step 158 and heated in steps 160 and 162. Thus, the desired regions of the capsular bag 304 are heated and adhere to the desired portions of the IOL 330.

Figure 4E:
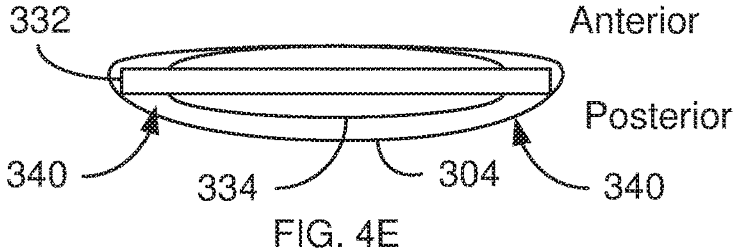
Figure 4F:
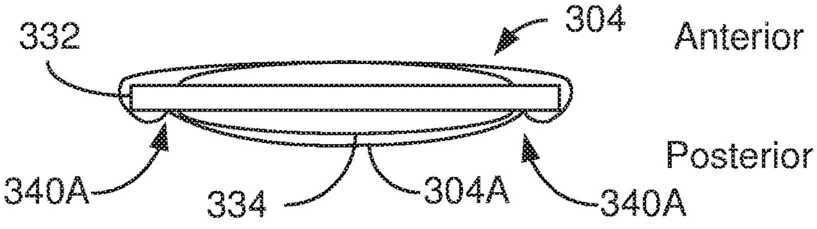

For example, FIG. 4E depicts a side view of the capsular bag 304 and the IOL 330 after the capsular bag 304 has collapsed. Thus, FIG. 4E may be considered a different view of the capsular bag 304 and IOL 330 shown in FIG. 4D. Also indicated are regions 340 that are to be sealed using the method 150. The anterior side (closer to the cornea 302) and posterior side of the optic 304 are also indicated. FIG. 4F depicts the capsular bag 304A and IOL 330 after the method 150 is completed. The capsular bag 304 has been sealed to the haptic 332 at selected locations 340A. A portion 304A of the capsular bag 304 thus seals the posterior surface of the optic 334. Consequently, the position of the IOL 330 in the capsular bag 304 is stabilized by the locations 340A at which the IOL is adhered to the capsular bag. As can be seen in FIG. 4F, the capsular bag 304 is bonded to the IOL 330 at locations 340A outside of the optic 334 and far from the optic axis.

Figure 5A:
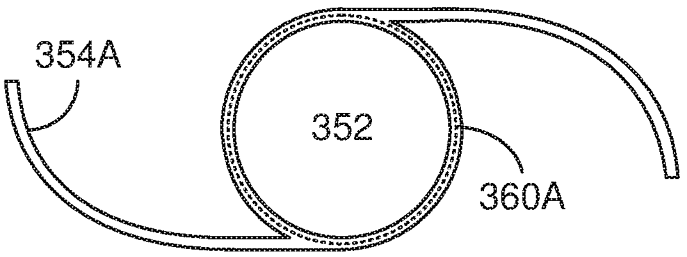
FIGS. 5A-5G depict exemplary embodiments of images of the IOLs configured to be used with non-surgical procedure for adhering the capsular bag to the IOL.

FIGS. 5A-5G depict various views of IOLs that may be used in conjunction with the methods 100 and/or 150. FIG. 5A depicts an IOL 350A including an optic 352 and a support structure 354A, or haptic 354A. In this embodiment, the optic 352 and haptic 354 may be formed of different materials. For example, the haptic 354 may be formed of hydrophilic material(s) or other materials that may provide a better bond to the heated capsular bag. In this embodiment, the capsular bag is desired to be bonded to the haptic 354A at region 360A shown by a dashed line. Thus, the posterior surface of the optic 352 may be sealed. Because of the seal at locations 360A, the haptic 354A can but need not include a sharp edge for mitigating PCO.

Figure 5B:
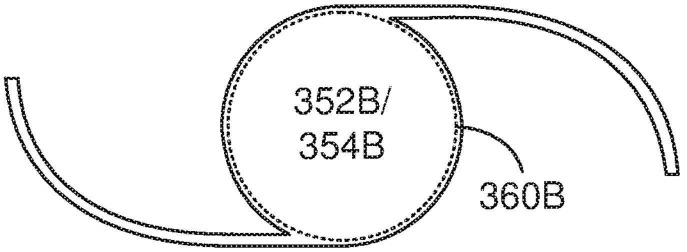

FIG. 5B depicts another embodiment of an IOL 350B including an optic 352B and a support structure 354B. In this embodiment, the optic 352B and haptic 354B may be formed of the same material(s). Thus, the optic 352B and haptic 354B may be molded together. In this embodiment, the capsular bag is desired to be bonded to the haptic 354B at region 360B shown by a dashed line. Thus, the posterior surface of the optic 352B may be sealed. Because of the seal at locations 360A, the haptic 354A can but need not include a sharp edge for mitigating PCO.

Figure 5C:
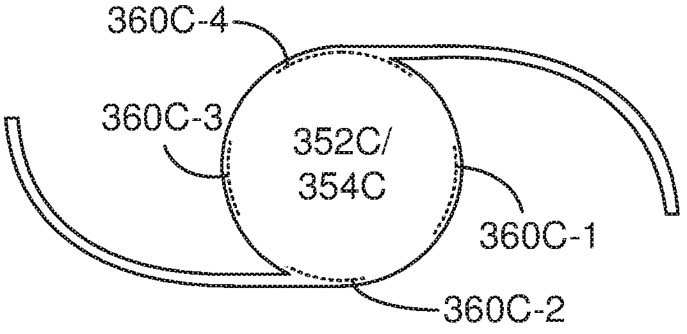

FIG. 5C depicts another embodiment of an IOL 350C including an optic 352C and a support structure 354C. In this embodiment, the optic 352C and haptic 354C may be formed of the same material(s). The capsular bag is desired to be bonded to the haptic 354C at regions 360C-1, 360C-2, 360C-3 and 360C-4, shown by dashed lines. Thus, the posterior surface of the optic 352C may not be sealed. Instead, the IOL 350C is merely desired to be stabilized in the capsular bag.

Figure 5D:
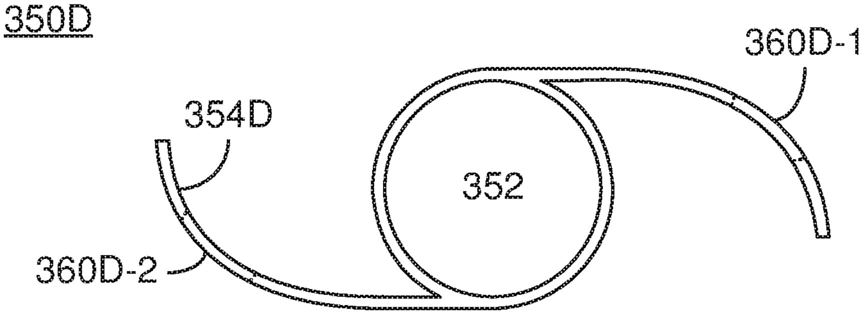

FIG. 5D depicts another embodiment of an IOL 350D including an optic 352D and a support structure 354D. In this embodiment, the optic 352D and haptic 354D may be formed of the same material(s). The capsular bag is desired to be bonded to the haptic 354D at regions 360D-1 and 360D-2, shown by dashed lines. Thus, the IOL is to be adhered to the capsular bag along the arms of the haptic 354D. The IOL 350C is thus stabilized in the capsular bag.

Figure 5E:
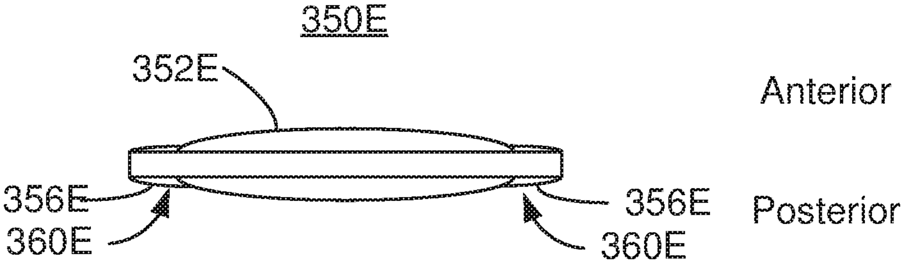

FIG. 5E depicts another embodiment of an IOL 350E including an optic 352E. Although not explicitly depicted in FIG. 5E, the IOL 350E additionally includes haptics extending from the periphery of optic 352E. In this embodiment, the capsular bag is desired to be bonded to the IOL 350E at regions 360E, which may be a region on the posterior surface of IOL 350E surrounding the periphery of optic 352E. Additionally, the capsular bag may be bonded to the haptics of IOL 350E. In certain embodiments, region 360E may include a coating 356E. The coating 356E may improve the bonding between the IOL 350E and the capsular bag. Thus, the coating 356E may be configured to bond to Type IV collagen that has been heated to the desired temperature range. After cooling, the coating 356E better adheres to the capsular bag. Thus, bonding between the IOL 350E and the capsular bag may be improved. As just one example, the coating may be Rose bengal stain, which may increase bonding when heated using green laser light.

Figure 5F:
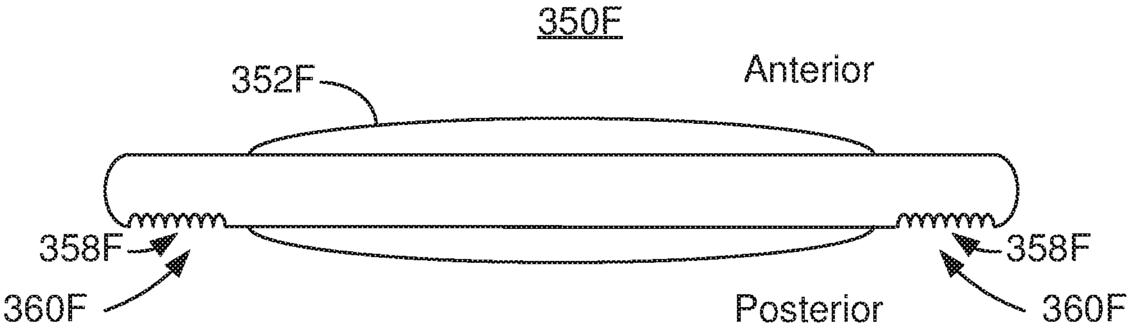

FIG. 5F depicts another embodiment of an IOL 350F including an optic 352F. Although not explicitly depicted in FIG. 5F, the IOL 350F additionally includes haptics extending from the periphery of optic 352F. In this embodiment, the capsular bag is desired to be bonded to the IOL 350F at regions 360F, which may be a region on the posterior surface of IOL 350E surrounding the periphery of optic 352E. IOL 350F may include structure 358F to improve ingress of melted collagen. Stated differently, the structure 358F is used to improve bonding between the IOL 350F and the capsular bag (not shown). In certain embodiments, the structure 358F may take the form of ridges or other texturing and may improve the bonding between the haptic 354F and the capsular bag. Thus, bonding between the IOL 350F and the capsular bag may be improved.

Figure 5G:
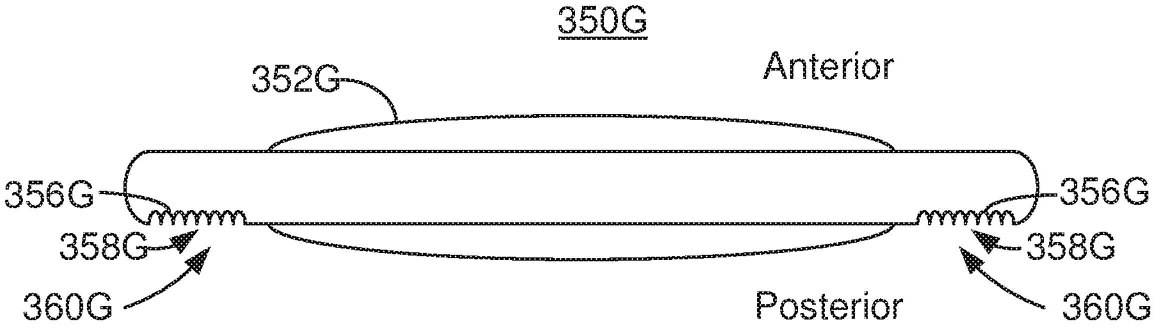

FIG. 5G depicts another embodiment of an IOL 350G including an optic 352G. Although not explicitly depicted in FIG. 5G, the IOL 350G additionally includes haptics extending from the periphery of optic 352G. In this embodiment, the capsular bag is desired to be bonded to the IOL 350G at regions 360G, which may be a region on the posterior surface of IOL 350G surrounding the periphery of optic 352G. IOL 350G may include both a coating 356G to improve bonding (as described above with regard to FIG. 5E) and structure 358G to improve ingress of melted collagen (as described above with regard to FIG. 5F).

It will be appreciated that various of the above-disclosed and other features and functions, or alternatives thereof, may be desirably combined into many other different devices or applications. It will also be appreciated that various presently unforeseen or unanticipated alternatives, modifications, variations or improvements therein may be subsequently made by those skilled in the art which alternatives, variations and improvements are also intended to be encompassed by the following claims.

I claim:

1. A method for performing an ophthalmic procedure on an eye including a capsular bag, the eye having an intraocular lens (IOL) comprising an attachment feature implanted therein, the method comprising:

identifying a peripheral area of a posterior portion of the capsular bag, the peripheral area adjacent to at least a portion of the attachment feature of the IOL; and applying laser energy to the peripheral area of the posterior portion of the capsular bag, the laser energy melting the peripheral area of the posterior portion of the capsular bag without cauterization and without forming a hole in the capsular bag such that the peripheral area of the posterior portion of the capsular bag adheres to the at least a portion of the attachment feature of the IOL while a central area of the posterior portion of the capsular bag remains intact.

2. The method of claim 1, wherein the eye has an optical path and wherein the peripheral area of the posterior portion of the capsular bag is outside the optical path.

3. The method of claim 1, further comprising determining an amount of the laser energy based on at least one melting temperature of the capsular bag, the melting temperature being determined based on an age of a patient having the eye.

4. The method of claim 1, wherein the attachment feature of the IOL comprises a coating configured to increase adherence to the capsular bag.

5. A system for performing an ophthalmic procedure on an eye including a capsular bag, the eye having an intraocular lens (IOL) implanted therein, the system comprising:

a laser;

a data processing unit for receiving an image of at least a portion of the eye and determining a portion of the capsular bag to adhere to an adjacent portion of the IOL comprising an attachment feature; and a control unit configured to communicate with the laser and the data processing unit, the control unit configured to execute instruction for controlling the laser such that the laser applies laser energy to melt the portion of the capsular bag without cauterization and without forming a hole in the capsular bag such that the portion of the capsular bag adheres to the attachment feature of the adjacent portion of the IOL.

6. The system of claim 5, wherein the IOL includes an optic having a posterior surface and wherein the adjacent portion of the IOL comprises a portion of a periphery of the posterior surface of the optic.

7. The method of claim 1, wherein the attachment feature of the IOL comprises a structure configured to facilitate ingress of a melted component of the capsular bag.

8. The method of claim 1, wherein the peripheral area abuts at least a portion of the attachment feature of the IOL.

9. The system of claim 5, wherein the portion of the capsular bag abuts the adjacent portion of the IOL.

10. The method of claim 1, wherein the applying the laser energy to the peripheral area of the posterior portion of the capsular bag is performed between forty-eight hours and two weeks after the IOL is implanted in the eye.

* * * * *